(12) United States Patent
Frid

(10) Patent No.: US 6,389,946 B1
(45) Date of Patent: May 21, 2002

(54) METHOD FOR MANUFACTURING BRAIDED MULTIFILAMENT STRUCTURES FOR AN ENDOPROSTHESIS FOR RAMIFICATION OF AN ANATOMICAL CONDUIT

(75) Inventor: Noureddine Frid, Beersel (BE)

(73) Assignee: Medicorp R & D Benelux S.A., Mons (BE)

(*) Notice: Subject to any disclaimer, the term of this patent is extended or adjusted under 35 U.S.C. 154(b) by 0 days.

(21) Appl. No.: 09/684,438

(22) Filed: Oct. 10, 2000

Related U.S. Application Data (62) Division of application No. 09/007,828, filed on Jan. 15, 1998.

(30) Foreign Application Priority Data

Jan. 16, 1997 (BE) .......................................... 09700043

(51) Int. Cl.[7] .................................................. D04C 1/06
(52) U.S. Cl. .......................................... 87/11; 623/1.53
(58) Field of Search ............................... 87/11; 623/1.53

(56) References Cited

U.S. PATENT DOCUMENTS

| | | | |
|---|---|---|---|
| 3,586,058 A | * | 6/1971 | Ahrens ........................ 138/103 |
| 4,425,908 A | | 1/1984 | Simon |
| 4,503,569 A | | 3/1985 | Dotter |
| 4,512,338 A | | 4/1985 | Balko et al. |
| 4,580,568 A | | 4/1986 | Gianturco |
| 4,655,771 A | | 4/1987 | Wallsten |
| 4,665,906 A | | 5/1987 | Jervis |
| 4,681,110 A | | 7/1987 | Wiktor |
| 4,743,251 A | | 5/1988 | Barra |
| 4,795,458 A | | 1/1989 | Regan |
| 4,954,126 A | | 9/1990 | Wallsten |
| 5,037,427 A | | 8/1991 | Harada et al. |
| 5,061,275 A | | 10/1991 | Wallsten |
| 5,066,028 A | * | 11/1991 | Well ........................... 277/181 |
| 5,067,957 A | | 11/1991 | Jervis |
| 5,190,546 A | | 3/1993 | Jervis |
| 5,197,978 A | | 3/1993 | Hess |
| 5,201,901 A | | 4/1993 | Harada et al. |

(List continued on next page.)

FOREIGN PATENT DOCUMENTS

| | | |
|---|---|---|
| EP | 1205743 | 9/1970 |
| EP | 0730848 | 2/1996 |
| EP | 0740928 | 3/1996 |
| EP | 0744164 | 5/1996 |
| WO | 9219310 | 11/1992 |
| WO | 9530385 | 11/1995 |
| WO | 9531945 | 2/1996 |
| WO | 9713475 | 4/1997 |

*Primary Examiner*—Andy Falik
(74) *Attorney, Agent, or Firm*—Roylance, Abrams, Berdo & Goodman, L.L.P.

(57) ABSTRACT

A method for manufacture of braided multifilament structures for an endoprosthesis for ramification of an anatomical conduit. The method includes the operation of braiding filaments, made of a matter chosen from among the biocompatible elastic, superelastic and shape-memory materials, around a first mandrel, along the length of the first mandrel whose diameter corresponds to a branch of a base element. The method further includes setting up at least one auxiliary mandrel parallel to the first mandrel. The auxiliary mandrel includes a first end and a second end, of cross-section corresponding to those of a lumen. The first end is inserted in a straight line with the braid in progress, upstream of the braiding point, and the assembly has a cross-section corresponding to that of a trunk of a base element. The method further includes continuing the braiding around the assembly along a length corresponding to at least that of the trunk of a base element.

8 Claims, 9 Drawing Sheets

U.S. PATENT DOCUMENTS

| | | |
|---|---|---|
| 5,226,913 A | 7/1993 | Pinchuk |
| 5,354,309 A | 10/1994 | Schnepp-Pesch et al. |
| 5,361,674 A * | 11/1994 | Akiyama et al. ................. 87/9 |
| 5,395,390 A | 3/1995 | Simon |
| 5,405,377 A | 4/1995 | Cragg |
| 5,540,712 A | 7/1996 | Kleshinski |
| 5,540,713 A | 7/1996 | Schnepp-Pesch et al. |
| 5,554,181 A | 9/1996 | Das |
| 5,562,725 A | 10/1996 | Schmidt et al. |
| 5,562,728 A | 10/1996 | Lazarus et al. |
| 5,575,818 A | 11/1996 | Pinchuk |
| 5,597,378 A | 1/1997 | Jervis |
| 5,630,840 A | 5/1997 | Mayer |
| 5,674,277 A | 10/1997 | Freitag |
| 5,737,991 A * | 4/1998 | Kite, III .......................... 87/9 |
| 5,741,333 A | 4/1998 | Frid |
| 5,939,216 A * | 8/1999 | Kameda et al. ............. 428/698 |

* cited by examiner

Fig. 15 PRIOR ART

METHOD FOR MANUFACTURING BRAIDED MULTIFILAMENT STRUCTURES FOR AN ENDOPROSTHESIS FOR RAMIFICATION OF AN ANATOMICAL CONDUIT

This is a divisional of U.S. patent application Ser. No. 09/007,828, filed Jan. 15, 1998, the entire content of which is incorporated herein by reference.

FIELD OF THE INVENTION

The invention relates to luminal endoprostheses for ramifications (also called branchings or bifurcations) of anatomical conduits in mammals, especially humans.

The endoprosthesis according to the invention concerns more especially the vascular system and the cardiovascular system where, at various sites, there are branchings, ramifications or bifurcations, the essential function of which is to provide a balanced supply of blood to the organs, muscle tissues and connective tissues.

The circulation of the blood in the vessels raises numerous problems associated with hydrodynamics and due to the structure and, in general, the shape of these vessels.

Physiologists and morphologists generally accept that the disposition of the vessels is such that the circulation necessitates, mechanically, a minimum level of stress and that the surface of the walls adopts a minimum value.

BACKGROUND OF THE INVENTION

The luminal endoprostheses which have been developed to date generally assume simple tubular or cylindrical shapes or, more rarely, a hyperboloid shapes. Such prostheses are described in particular in the documents WO-A-83/03752 and GB-A-1 205 743.

These prostheses include a tubular braided structure for an arterial conduit or other conduit and are put into place, after compression of their diameter, using a tubular applicator. These prostheses are not intended for implantation in a bifurcated shape.

Attempts have been made to develop bifurcated shapes of prostheses. These essentially concern the junction of the abdominal aorta, which is a large vessel, but investigations are in their infancy.

A bifurcated prosthesis for implantation in a conduit such as a blood vessel is known, in particular, from U.S. Pat. No. 4,994,071.

This prosthesis, made up of interconnected metal rings, comprises a trunk formed by a first series of interconnected rings, and at least one branch formed by a second series of interconnected rings, these at least two series being connected to each other via a flexible element, folded in such a way as to correspond to the angle between the ramifications in question. Putting such a prosthesis into place is extremely difficult, or even impossible.

U.S. Pat. No. 5,609,605 describes a bifurcated endoprosthesis made out of two single balloon endoprostheses of variable diameter placed side-by-side in a bifurcated lumen.

Documents EP-A-0 539 237 and WO 96/34580 describe devices for putting bifurcated endoprostheses into place. These endoprostheses include a main body (trunk) and two members (branches) extending from the main body; they are made of woven, folded or pleated fibre. Placing such endoprostheses in arterial bifurcations is a long and delicate operation, especially on account of stringent requirements in respect of orientation and positioning. Furthermore, the angle provided by the two branches does not necessarily correspond to the original angle between the vessels.

Document EP-A-0 461 791 illustrates the difficulties involved in putting a bifurcated prosthesis into place, even in the case of an aneurysm of the abidominal aorta, where the vessels are of a large diameter.

Other documents as U.S. Pat. Nos. 5,609,627 and 5,639, 278 describe trouser-form endoprostheses with added legs, which often cause blood flow perturbation.

The bifurcation anglers differ from one person to the next and from one population to another. They are smaller and more asymmetrical in the elderly than in younger subjects. The bifurcations are more asymmetrical in men than in women. Comparative studies have shown that the bifurcation angles in Asiatics are wider than in Caucasians.

Hydrodynamics also teaches that the thicknesses of the arterial walls differ from one population to another. When these walls are thin, the effort necessitated by the transport of the blood increases. It is also known that when the vessels are too large, the volume of blood increases beyond what is necessary. These factors promote aneurysms (dilation of the arterial wall).

The considerations detailed above show that it would be necessary to adapt the design of a bifurcation to each anatomical site, and also that this design must take into account the differences between different types of populations, between men and women, between the young and the elderly, etc. In practice, it is not possible to provide bifurcations tailored to each patient. This would in fact risk causing problems associated with waiting periods and prohibitive costs.

SUMMARY OF THE INVENTION

It has therefore been sought to develop a luminal endoprosthesis which can adapt to practically all the ramifications of the anatomical conduits, and in particular to those of the vascular and cardiovascular system.

Another object of the invention is that this endoprosthesis should be easy to put into place.

Another object is to afford the possibility of placing such an endoprosthesis at sites which have hitherto been inaccessible.

The subject of the invention is a luminal endoprosthesis for ramification of an anatomical conduit, including at least one radially compressible and extendable tubular structure which comprises at least one base element comprising a continuous multifilament structure with N filaments delimiting a longitudinal cavity open at its two ends. This at least one base element comprises two flexible segments, respectively a first segment and a second segment, extending one in a continuation of the other, substantially along the same axis in the absence of stress, and at least one lumen opening into the longitudinal cavity at the junction between the first segment and the second segment, the same metal filaments forming the structure of the first segment and of the second segment.

According to a first preferred embodiment, the first element (or trunk) has a greater cross-section than that of the second segment (or branch). According to a second preferred embodiment, the first segment and the second segment of one base element have cross-sections which are practically identical.

This endoprosthesis generally comprises two base elements, the respective first segments of each of these two base elements being able to be engaged one within the other, and assuming, in this position, cross-sections which are in essence identical, the second segment of one of the base elements being engaged in a lumen of the other base element.

At least one of the base elements advantageously comprises a sleeve made of biocompatible material, such as a polymer of the polyester, polyurethane or polyethylene type, or another type of biocompatible material.

The structure of each base element can be braided using metal filaments made of an alloy for medical use or shape-memory filament.

The first segment of each of the two base elements can comprise a part of greater cross-section.

According to one embodiment, the second segment of at least one of the base elements comprises a part of greater cross-section. In the absence of stress, the filaments of the braided structure intersect at an angle and a diameter which vary depending on the desired application.

In a preferred manner, the cross-section of the trunk of a base element is equal to at least 4 times that of its branch and/or a lumen of a base element has a cross-section at least equal to ¼ that of the trunk or at least equal to that of the branch.

Another subject of the invention is a method for manufacture of braided multifilament structures for an endoprosthesis as described herein above, and which method comprises the following operations:

braiding of filaments, made of a biocompatible elastic, shape-memory or superelastic material, around a first mandrel, along the length and the diameter corresponding to the branch of a base element, setting up at least one auxiliary mandrel parallel to the first mandrel, the said auxiliary mandrel including a first end and a second end, of cross-section corresponding to those of a lumen, the said first end being inserted in a straight line with the braid in progress, upstream of the braiding point, the assembly (first mandrel—auxiliary mandrel) having a cross-section corresponding to that of a trunk of a base element, continuing the braiding around the assembly along a length corresponding to at least that of the trunk of a base element.

This method may additionally comprise the following operation:

continuing the braiding around the assembly (first mandre—auxiliary mandrel) along a length corresponding to at least twice that of the trunk of a base element, separating the second end of the at least one auxiliary mandrel from the first mandrel, the said second end having a cross-section corresponding to that of a lumen of a base element, continuing the braiding on the first mandrel, along a length and a diameter corresponding to the branch of a base element, disengagement of the obtained braid and of the mandrels, cutting the obtained braid into two distinct base elements.

When the auxiliary mandrel comprises at least one flexible part, the separation between the second end of the auxiliary mandrel and the main mandrel can be effected by folding down the said second end on the braid in progress.

In addition, at least one widening part can be placed on the said first mandrel along the length corresponding to one of the future branches.

A widening part, of diameter greater than the assembly (first mandrel—auxiliary mandrel), can be placed on this assembly along the length corresponding to the future trunks. The method of manufacture, such as described, can comprise the insertion of a single auxiliary mandrel or of two auxiliary mandrels.

The invention also relates to a method for manufacture of braided multifilament structures for the base element of an endoprosthesis such as described herein above, which method comprises the following operations:

braiding of filaments, made of biocompatible elastic, superelastic or shape-memory material, around a first mandrel, along the length and the diameter corresponding to one of the segments of the base element, setting up an auxiliary mandrel perpendicular to the first mandrel, the said auxiliary mandrel having a cross-section corresponding to those of the desired lumen of the said auxiliary mandrel, the said auxiliary mandrel being inserted at the level of the braiding point of the braid in progress, continuing the braiding around the assembly (first mandrel—auxiliary mandrel) along a length corresponding at least to that of the contact (first mandrel—auxiliary mandrel), continuing the braiding on the first mandrel, along a length corresponding to the other segment of the base element, disengagement of the obtained braid and of the first mandrel. The setting up of an auxiliary mandrel is advantageously repeated during the braiding of the element in such a way as to form several distinct lumens.

When shape-memory filaments are used, the above operations are completed by the thermal operations required for the metal to memorize a predetermined nominal shape.

An advantage of the endoprosthesis according to the invention is that it adapts to virtually any type of branching or ramification, particularly of the arterial system, and to any angle, and this irrespective of the age and sex of the subject and the population to which the subject belongs; it is thus universal.

The developed endoprosthesis shape is simple and flexible, and it thus matches the anatomical site as it is, by which means it is possible to avoid the problems of positioning, migration, thrombosis and adaptation to the geometry of the original ramification of each patient.

The endoprostheses according to the invention can be made with numerous variations in terms of cross-section, length, and angle of intersection of the filaments, and they can be made of numerous materials.

The endoprostheses according to the invention can be made on machines currently used for obtaining traditional tubular endoprostheses.

BRIEF DESCRIPTION OF THE DRAWINGS

Other features and advantages of the invention will be evident from the following description of various embodiments, applied here to the blood system, with reference being made to the attached figures, of which.

DESCRIPTION OF THE EMBODIMENTS

Figure 1:
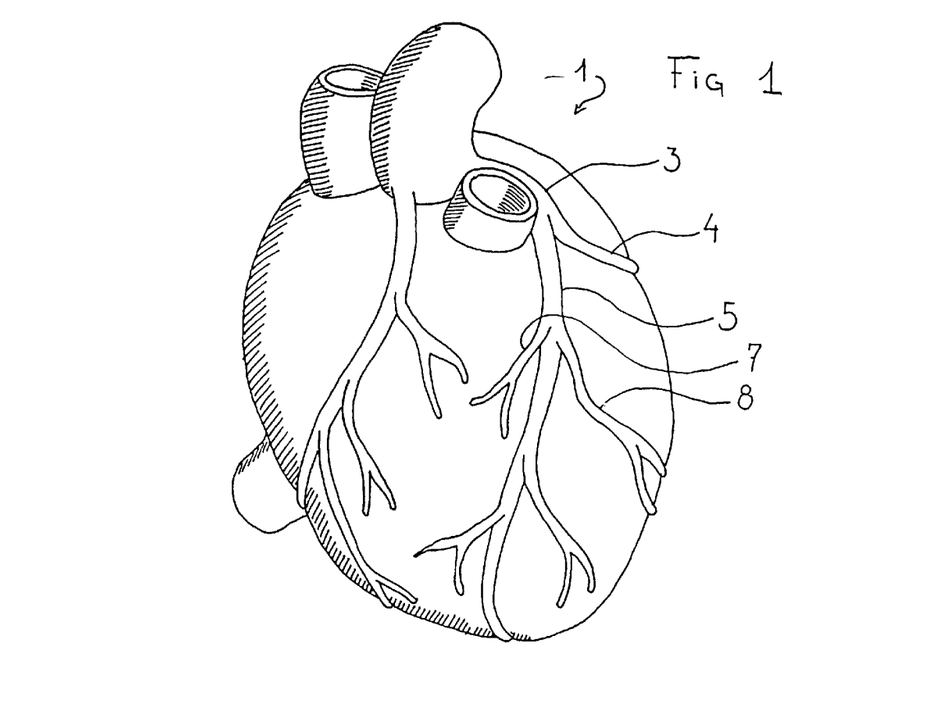
FIG. 1 is a diagrammatic view of a part of the vascular system including a typical series of configurations of ramifications.
Figure 2:
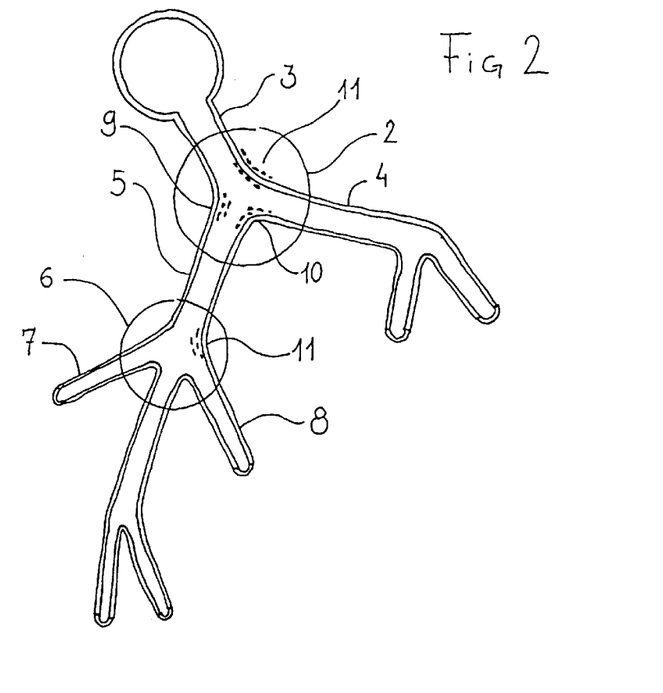
FIG. 2 is a general perspective view of an anatomical ramification.

FIG. 1 shows, in diagrammatic representation, a site presenting typical ramifications, represented in detail in FIG. 2.

The figure distinguishes in particular the site 2 consisting of the "Y" bifurcation of the main left trunk 3 towards the left circumflex artery 4 and the anterior left coronary artery 5.

At the site 6, two branches, namely 7 (the descending anterior left coronary artery) and 8 (the left circumflex), join the anterior left coronary artery 5 at the same level, forming a "Ψ" ramification.

For the small arteries, there is a close relationship between the velocity of the blood and the dimension of the arteries. The smaller the diameter, the lower the velocity of the blood and the greater the tendency of the artery to become blocked.

By contrast, when the vessels are too large, the volume of blood increases to beyond what is necessary. This factor promotes aneurysms (dilation of the arterial wall). The geometry of the various bifurcated forms influences the blood flow, especially at the site of the ramification, by slowing it down and by creating local turbulence.

Research undertaken by several investigators has demonstrated that there is a relationship between the high velocity of the blood, the shear stress at the site of the ramification, and the appearance of sclerotic lesions along the arterial wall.

FIG. 2 thus shows the stress zones particular to a "Ψ" bifurcation, namely a zone of low shear 9 (low frequency zone) and a zone of high shear 10 in the fork.

It is also known that the vibration of the artery at low frequency, due to the low velocity of the blood, can be highly destructive for the artery. It should also be noted that in elderly subjects, the angle of branching of the ramifications becomes smaller with age and as a result can form an atheroma 11. The same phenomenon can appear on the iliac arteries.

Figure 3:
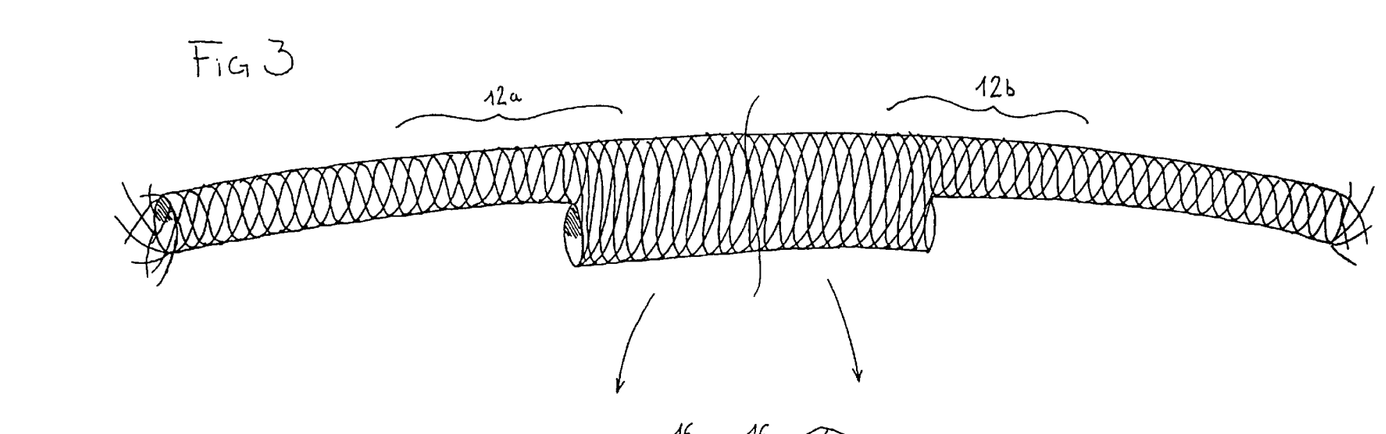
FIGS. 3 and 4 are diagrammatic perspective views of two base elements (joined, then separated) of the endoprosthesis according to the invention.
Figure 4:
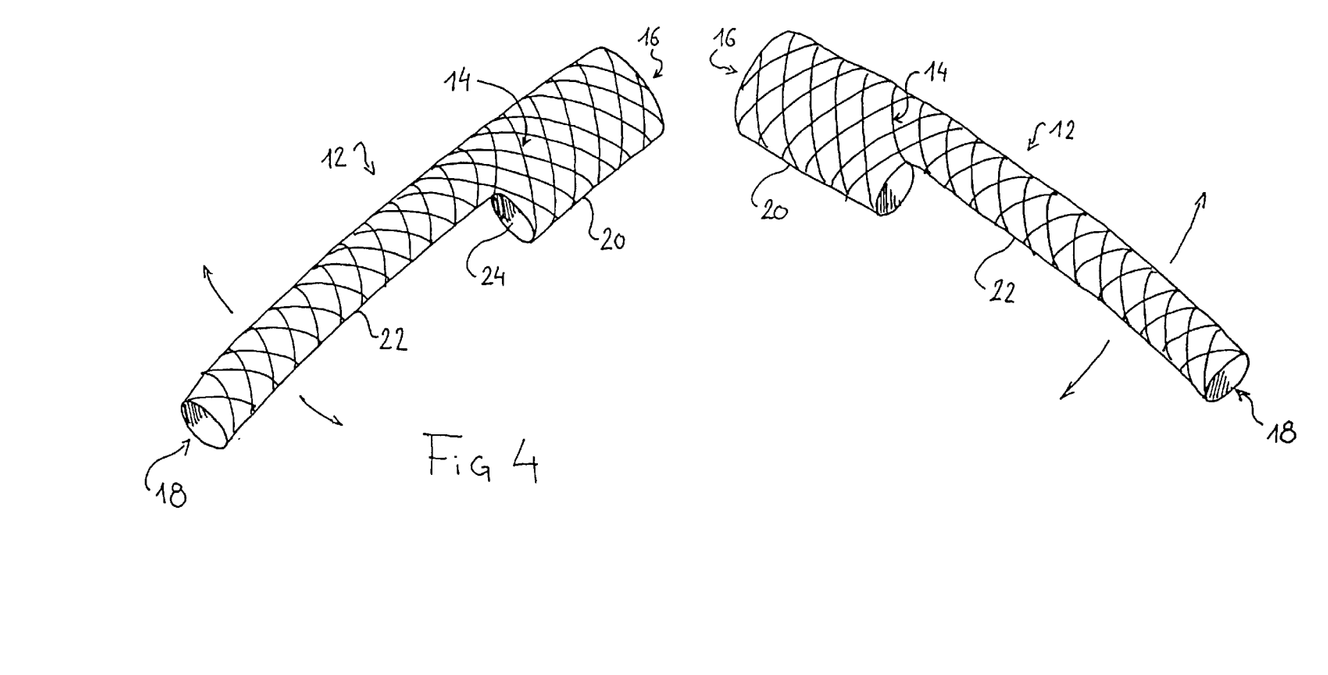

FIGS. 3 and 4 show, in perspective, the structures of two base elements 12 of the endoprosthesis according to the invention.

In FIG. 3, the structures of these base elements are still joined (12a, 12b) in connection with a method of manufacture which will be described hereinafter.

FIG. 4 shows the structures of these base elements 12a and 12b separated.

Each base element 12 comprises a braided multi-filament structure which delimits a longitudinal cavity 14 open at its two ends 16, 18.

Each base element 12 is made up of two segments, referred to hereinafter as first segments or "trunks" 20 and second segments or "branches" 22 (the trunks 20 in FIG. 4 each have a greater cross-section than the corresponding branches 22).

A lumen 24 is formed in each base element 12 and opens into the longitudinal cavity 14 at the level of the junction between the two segments 20, 22.

The structure of each base element 12 is here formed by N braided filaments in two layers (each layer being formed by N/2 filaments). The N filaments of the structure of each base element 12 extend without interruption from one end to the other (16, 18) of this element 12, the embrasure of each lumen 24 thus being "braided" in each structure.

Each structure is braided with metal filaments made of resilient alloy for medical use or shape-memory filament; by applying to it an external stress, it can be compressed to a fraction of its initial diameter (the reduction in the diameter being accompanied by a proportional longitudinal elongation), and in this state it can be introduced, via an applicator known per se, through an incision and into the subject's circulatory system, at the appropriate site.

In the uncompressed state, that is to say before the endoprosthesis has been put into place, or when the endoprosthesis is in place, the filaments forming the two layers intersect to form an angle which is such that it is possible to obtain a good compromise, from the mechanical point of view, between the resistance to radial compression and the flexibility of the endoprosthesis.

Figure 5:
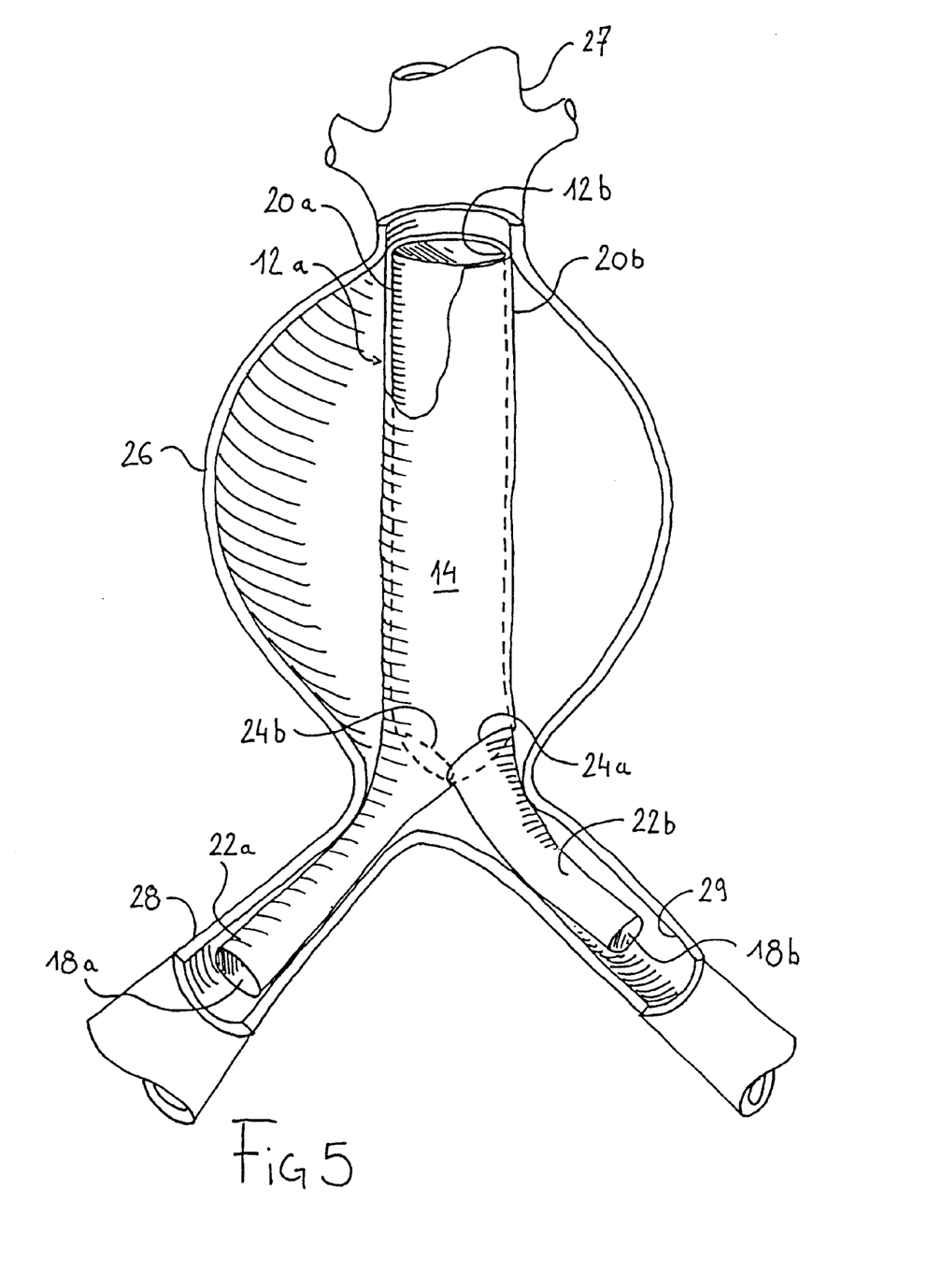
FIG. 5 is a perspective cutaway view of an endoprosthesis placed in an aneurysm (of the abdominal aorta)

FIG. 5 shows the arrangement of an endoprosthesis 25 placed in an aneurysm 26 of the abdominal aorta 27.

As indicated hereinabove, a first base element 12a is introduced through an incision into one of the iliac arteries 28. The applicator (not shown) is inserted as far as the abdominal aorta 27, upstream of the aneurysm 26. The applicator is gradually withdrawn, leaving in place the element 12a, the trunk 20a of which lines the aorta 27 at the level of the aneurysm 26, and the branch 22a in the iliac artery 28. The angle between the trunk 20 and the branch 22 of the base element 12a adapts automatically to the physiological divergence between the abdominal aorta 27 and the iliac artery 28.

The lumen 24a of the first base element 12a is disposed in line with the mouth of the other iliac artery 29.

A second base element 12b is introduced via the other iliac artery 29 and the lumen 24a in the trunk 20a. When the endoprosthesis is in place, the two trunks 20a and 20b are thus engaged one within the other, the branch 22b of the second element reaching into the iliac artery 29.

The two branches 22a and 22b, being flexible, spontaneously assume the angle of the original physio-logical ramification.

The two lumens 24a and 24b, disposed opposite one another, do not induce any turbulence or any relative loss of pressure between the two blood vessels. The endoprosthesis thus fully assumes the same functions as a healthy ramification.

The structure of the endoprosthesis around the lumens 24a, 24b is strong and stable, thereby avoiding that these lumens be crushed, even during insertion inside the catheter.

The base element 12a is lined internally by a sleeve (not shown) made of biocompatible polymer material and intended to serve as a support for regeneration of the tissues. Because one of the two trunks 20a and 20b of the base elements 12 is engaged on the other one, this sleeve is sandwiched between the two structures, and this affords increased safety. The slight divergence of the filaments at the ends of each structure (as is shown in FIG. 3) provides for an excellent anchoring of the endoprosthesis in the body tissues and a stability due to the engagement of the two trunks 20a and 20b.

Figure 6:
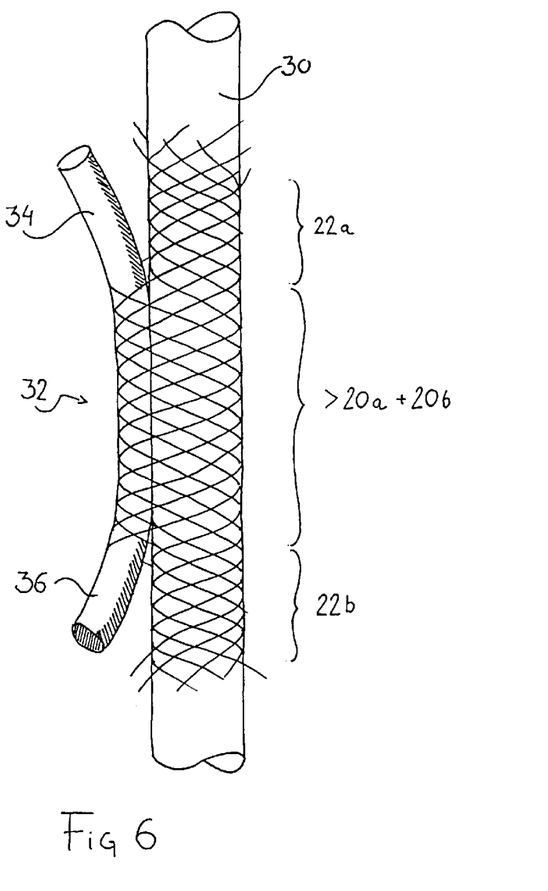
FIG. 6 is a perspective view of a stage in the manufacture of base element structures of the endoprosthesis.

FIG. 6 illustrates a method specially developed for the manufacture, by braiding, of base element structures 12 of the endoprosthesis 25. This method allows two base elements of corresponding dimensions to be produced in a single operation.

The method begins with a conventional braiding operation: N filaments are interlaced in two layers, in opposite directions, around a first cylindrical mandrel 30. This braiding, at the diameter of a branch 22a of a base element 12a, is continued along a length corresponding to that of the desired branch 22a. An auxiliary mandrel 32 is then arranged parallel to the first mandrel 30; one end 34 of the auxiliary mandrel 32, whose cross-section in relation to that of the desired lumen 24, is placed against the braid in progress.

The braiding of the N filaments is continued, this time around the assembly {first mandrel 30—auxiliary mandrel 32}, along a length corresponding at least to that of two trunks 20a, 20b of base elements 12a, 12b.

When the desired length has been reached, the end 36 of the auxiliary mandrel 32 is drawn away from the first mandrel 30.

For the mandrel 32, it is possible to use a flexible material or a bendable form: in this case, the mandrel is drawn away by simply folding this end 36 back onto the braid in progress.

The braiding is then continued on the first mandrel 30 along a length corresponding to that of the branch 22b of the base element 12b.

After separation from the mandrels, the braid presents the appearance shown in FIG. 3. It allows two structures as represented in FIG. 4 to be obtained.

The method described permits great variety in the shapes of the base elements 12, and, consequently, the endoprostheses made with different base elements 12 are adapted to practically all the anatomical sites.

It has to be stressed that the base elements are formed in one single operation while known bifurcated stents have to be assembled.

Figure 7:
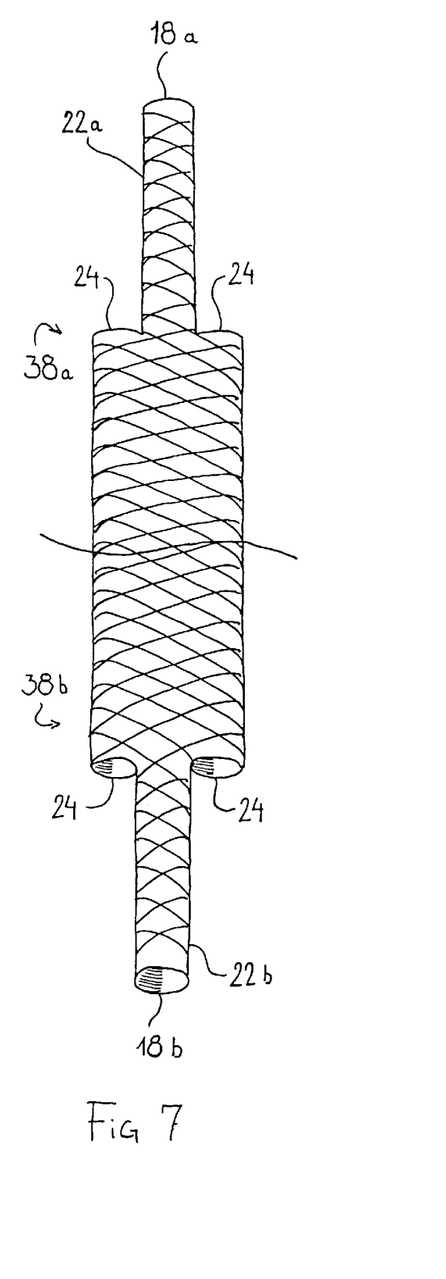
FIG. 7 is a perspective view of an alternative manufacture of base element structures.

The braid represented in FIG. 7 is made by using two auxiliary mandrels 32 of the same length. It is applied in the case of Ψ ramifications (as shown at the site 6 in FIG. 2) by combining two base elements 12 (see FIG. 4) with a base element 38 having two lumens 24. The superposition of the three layers of the trunks 20 of the base elements maintains the permeability of the artery.

Figure 8:
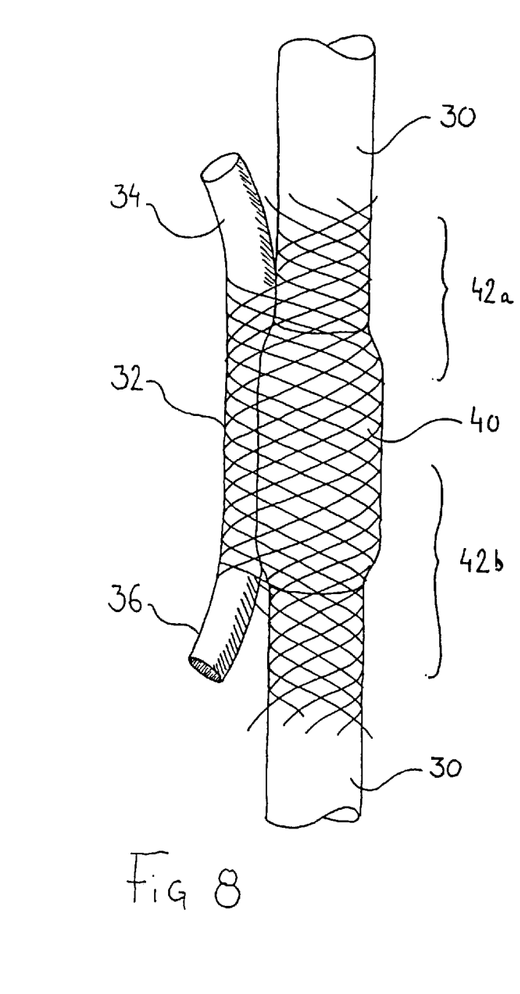
FIGS. 8 and 9 are perspective views during and after manufacture, respectively, of an alternative embodiment of base elements of the endoprosthesis.
Figure 9:
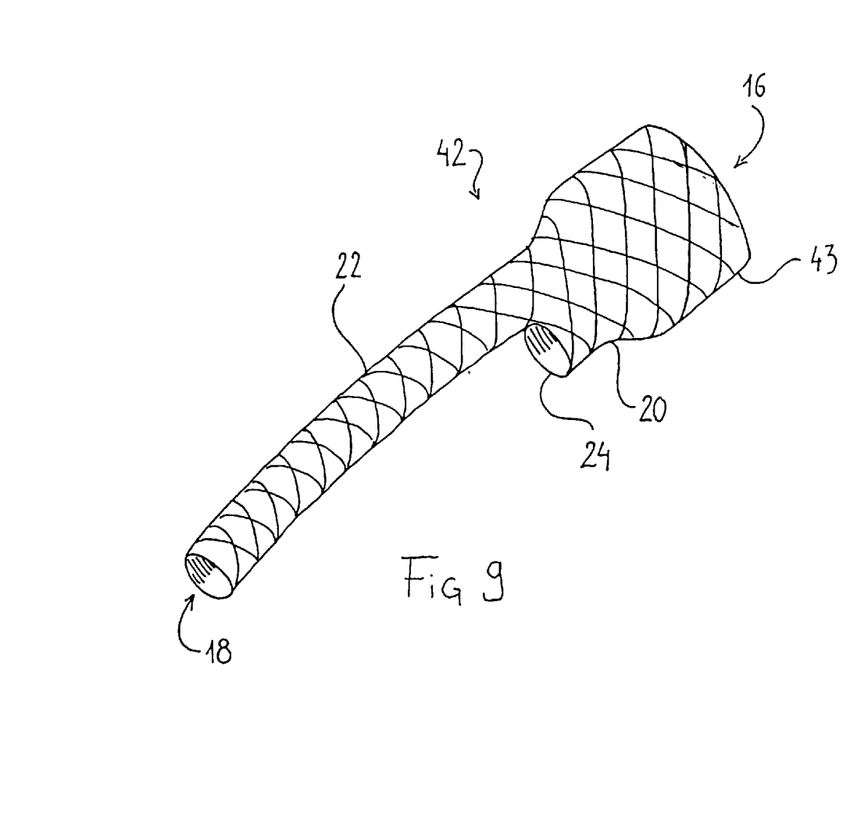
Figure 10:
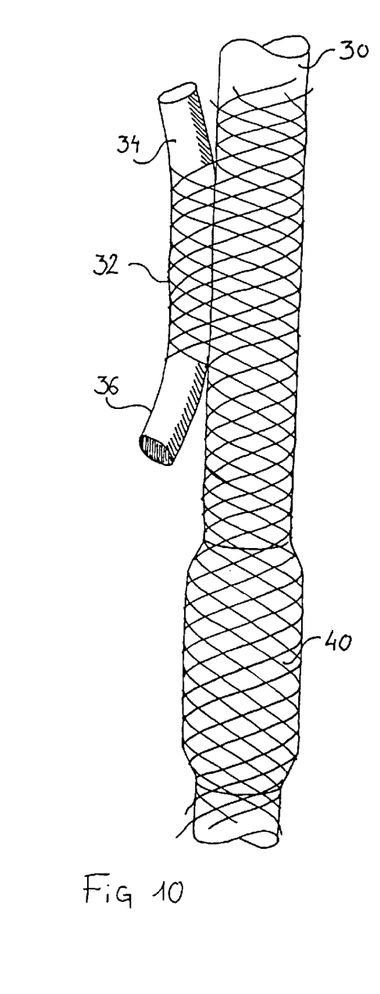
FIGS. 10 and 11 are perspective views during and after manufacture, respectively, of another alternative embodiment of base elements of the end-prosthesis.

FIG. 8 shows another variant of the method described. In this variant, use is made of a widening part 40 mounted on the first mandrel 30 level with the auxiliary mandrel 32. The shape of the base element 42 thus obtained, presents a widening 43, as can be seen in FIG. 9, by which means it it possible to compensate for a possible narrowing of a neck of an abdominal aneurysm.

Figure 11:
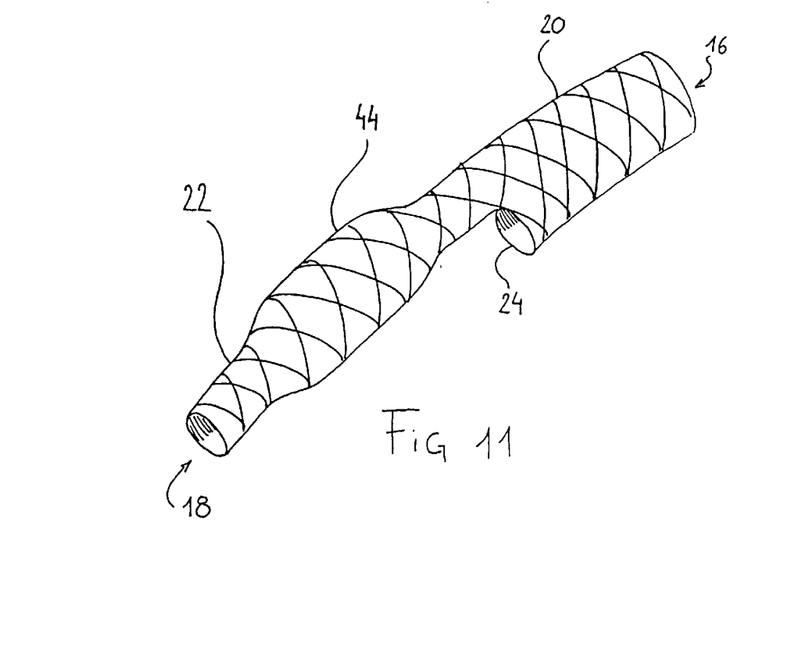

The widening part 40 can also be placed on the first mandrel 30 higher up or lower down than the auxiliary mandrel 32, as is represented in FIG. 11.

Figure 12:
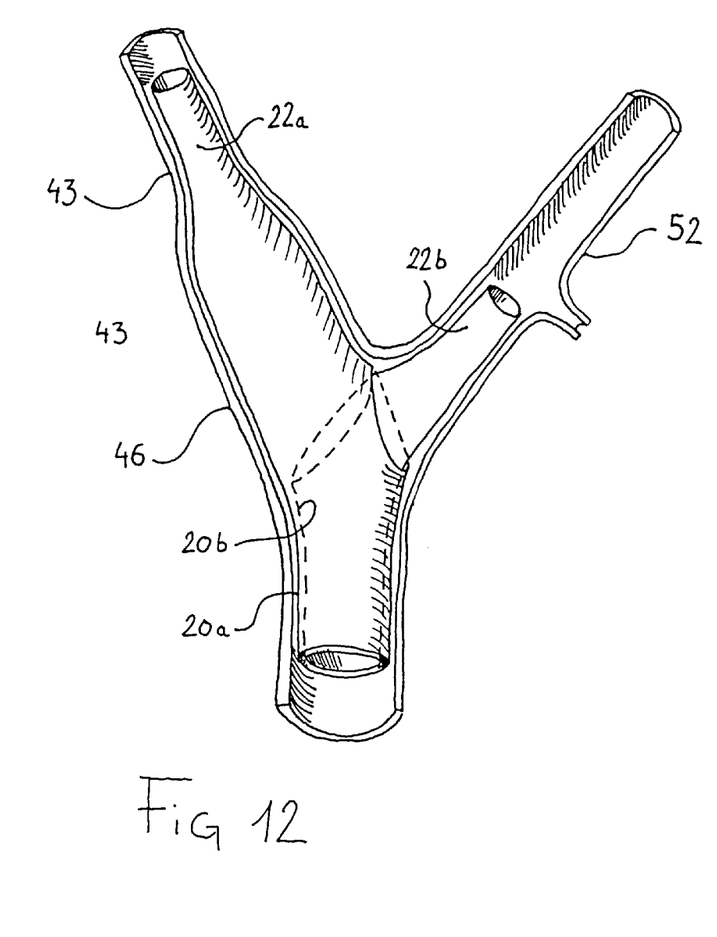
FIG. 12 is a perspective cutaway view of an endoprosthesis according to the invention after it has been placed in a bifurcation of the carotid.

The use of an endoprosthesis employing a base element presenting such a widening 43 is illustrated in FIG. 12: one of the base elements 12 presents a widening 43 which is made to coincide with the carotid sinus 46 in the bifurcation of the common carotid artery 48 into the internal carotid 50 and external carotid 52.

Figure 13:
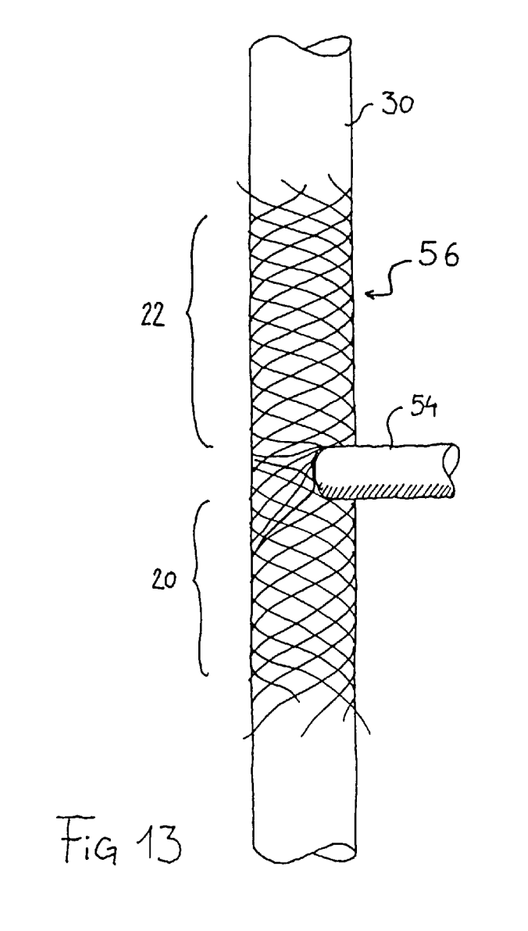
FIGS. 13 and 14 are perspective views during and after manufacture, respectively, of a third alternative embodiment of base elements of the end-prosthesis.

FIG. 13 illustrates another variant of the method, which variant is obtained by placing another auxiliary mandrel 54, whose cross-section corresponds to that of the desired lumen 24, almost perpendicular to the first mandrel 30. In the case shown, the first segment 20 and the second segment 22 present the same diameter, corresponding to that of the first mandrel 30. The embrasure of the lumen 24 is braided in the structure of the base element 56.

Figure 14:
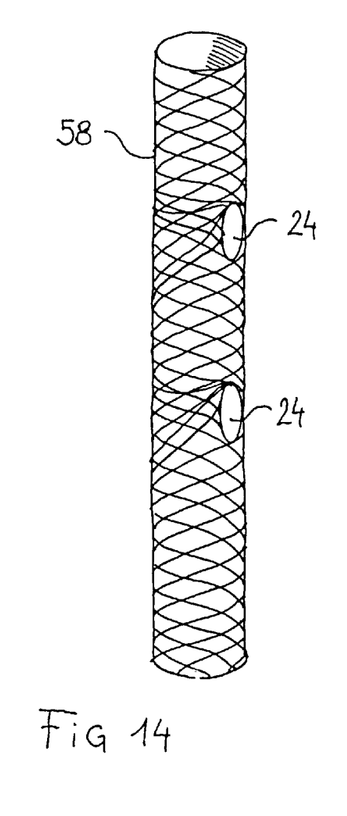

A base element 58, provided with two distinct lumens 24 disposed on the same generating line, is represented in FIG. 14. A base element 56, 58 can be used in combination with another base element 12 (see FIG. 4) especially for vessel shunts, the trunk 20 of the base element 12 having a cross-section in relation to one of the segments of the base element 56.

It goes without saying that, as a function of the configuration of the sites, the two variants of the method of manufacture can be combined with each other for production of complex endoprostheses.

Figure 16:
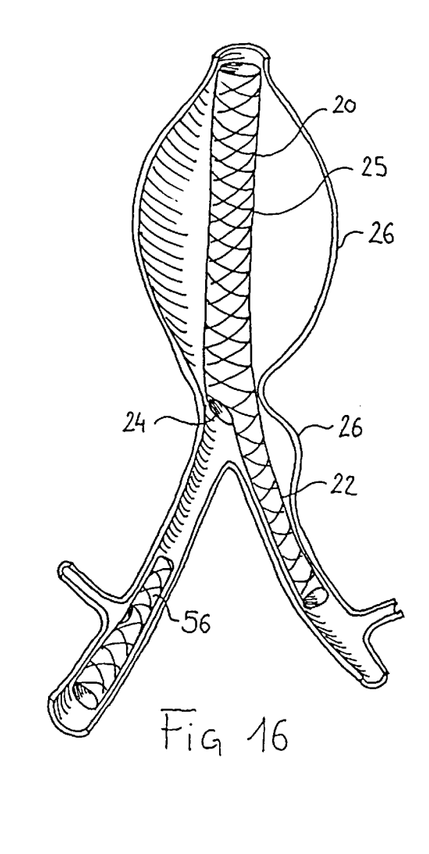

Two other ways of forming an endoprosthesis, each time using a single base element 12, 56, are illustrated in FIG. 16.

Figure 15:
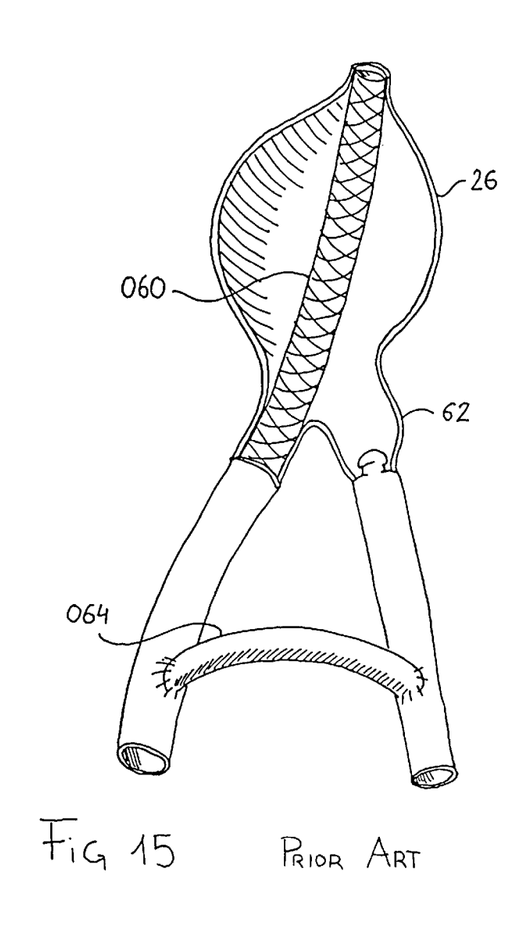
FIGS. 15 and 16 are diagrammatic perspective (cutaway) views of an aorto-iliac aneurysm, respectively with an endoprosthesis according to the prior art and with an endoprosthesis according to the invention.

By way of comparison, FIG. 15 shows a traditional operating procedure for this type of lesion (aneurysm) 26 which involves using an endoprosthesis of the prior art 060, and shutting down the affected section of vessel 62 and creating a bypass 064.

Though the present endoprothesis was described as self-expanding, it is obvious that the same principle applies to plastically deformable endoprotheses as e.g. endoprotheses associated with balloons.

What is claimed is:

1. A method for manufacture of braided multifilament structures for an endoprosthesis for ramification of an anatomical conduit, comprising the following operations:

braiding filaments, made of a material chosen from one of biocompatible elastic material, superelastic material and shape-memory material, around a first mandrel, along the length and the diameter corresponding to a branch of a base element, setting up at least one auxiliary mandrel parallel to the first mandrel, the said auxiliary mandrel including a first end and a second end, of cross-section corresponding to those of a lumen, the said first end being inserted in a straight line with the braid in progress, upstream of a braiding point, an assembly of the first mandrel and said at least one auxiliary mandrel having a cross-section corresponding to that of a trunk of a base element, and continuing the braiding around the assembly along a length corresponding to at least that of the trunk of a base element.

2. A method of manufacture according to claim 1, which additionally comprises the following operations:

continuing the braiding around the assembly along a length corresponding to at least twice that of the trunk of a base element, separating the second end of the at least one auxiliary mandrel from the first mandrel, the said second end having a cross-section corresponding to that of a lumen of a base element, continuing the braiding on the first mandrel, along a length and a diameter corresponding to the branch of a base element, to form an obtained braid, disengaging the obtained braid from the mandrels, and cutting the obtained braid into two base elements.

3. A method of manufacture according to claim 2, wherein the auxiliary mandrel comprises at least one flexible part, the separation between the second end of the auxiliary mandrel and the main mandrel being effected by folding down the said second end on the braid in progress.

4. A method of manufacture according to claim 2, which comprises inserting at least two auxiliary mandrels.

5. A method of manufacture according to claim 1, further comprising the following operation:

placing a widening part on the first mandrel along the length corresponding to a future segment of the base element.

6. A method of manufacture according to claim 1, further comprising the following operation:

placing a widening part, of diameter greater than the assembly, on this assembly along the length corresponding to future trunks of the base elements.

7. A method for manufacture of braided multifilament structures for a base element of an endoprosthesis for ramification of an anatomical conduit, comprising the following operations:

braiding of filaments, made of a material chosen from among one of biocompatible elastic material, superelastic material and shape-memory material, around a first mandrel, along the length and the diameter corresponding to one of first and second segments of the base element, setting up an auxiliary mandrel in essence perpendicular to the first mandrel, the said auxiliary mandrel having a cross-section corresponding to those of the desired lumen of the said base element, the said auxiliary mandrel being inserted at the level of a braiding point, continuing the braiding around the assembly along a length corresponding at least to that of contact between the first and auxiliary mandrels, continuing the braiding on the first mandrel, along a length corresponding to that of the other segment of the base element to form an obtained braid, and disengaging the obtained braid from the first mandrel.

8. A method of manufacture according to claim 7, wherein the setting up of an auxiliary mandrel is repeated during the braiding of the base element in such a way as to form several distinct lumens.

* * * * *